United States Patent [19]

Lewis et al.

[11] Patent Number: 5,612,336
[45] Date of Patent: Mar. 18, 1997

[54] HETEROCYCLIC AMIDE DERIVATIVES AS TACHYKININ ANTAGONISTS

[75] Inventors: Richard J. Lewis, Harlow; Angus M. MacLeod; Kevin J. Merchant, both of Bishops Stortford, all of United Kingdom

[73] Assignee: Merck, Sharp & Dohme Ltd., Hoddesdon, England

[21] Appl. No.: 373,195

[22] PCT Filed: Jul. 6, 1993

[86] PCT No.: PCT/GB93/01415

§ 371 Date: Jan. 13, 1995

§ 102(e) Date: Jan. 13, 1995

[87] PCT Pub. No.: WO94/01402

PCT Pub. Date: Jan. 20, 1994

[30] Foreign Application Priority Data

Jul. 13, 1992 [GB] United Kingdom ............ 9214864
Oct. 22, 1992 [GB] United Kingdom ............ 9222175
Dec. 14, 1992 [GB] United Kingdom ............ 9226070
Mar. 4, 1993 [GB] United Kingdom ............ 9304398

[51] Int. Cl.$^6$ .................. A61K 31/44; A61K 31/535; C07D 401/12; C07D 413/12

[52] U.S. Cl. .................. 514/235.2; 514/339; 540/585; 544/143; 544/373; 546/133; 546/201; 546/281.1; 546/337; 546/277.4; 548/312.1; 548/467

[58] Field of Search .......... 544/143; 546/277.4; 548/312.1, 467; 514/235.2

[56] References Cited

U.S. PATENT DOCUMENTS 5,328,927  7/1994  Lewis et al. .................. 549/467

FOREIGN PATENT DOCUMENTS

0333174A3  9/1989  European Pat. Off. .
0394989A3  10/1990  European Pat. Off. .

*Primary Examiner*—Robert W. Ramsuer
*Attorney, Agent, or Firm*—Robert J. North; Melvin Winokur

[57] ABSTRACT

Compounds of formula (I), and salts and prodrugs thereof, wherein $Q^1$ is phenyl substituted by one or more halo; optionally substituted naphthyl, indolyl, benzothiophenyl, benzofuranyl, benzyl or fluorenyl; the dotted line represents an optional covalent bond; one of X and Y is H and the other is hydroxy or $C_{1-6}$alkoxy, or X and Y together form a group =O or =NOR$^5$ where $R^5$ is H or $C_{1-6}$alkyl; $R^1$ is H or $C_{1-6}$alkyl. $R^2$ is CO—W—$R^6$ where W represents a bond or a hydrocarbon chain of 1–6 carbon atoms and $R^6$ is an azacyclic or azabicyclic group; $R^3$ is H, $C_{1-6}$alkyl or $C_{2-6}$alkenyl; and $R^4$ is phenyl optionally substituted by 1–3 of $C_{1-6}$ alkyl, $C_{2-6}$alkenyl, $C_{2-6}$alkynyl, halo, cyano, nitro, trifluoromethyl, trimethylsilyl, OR$^a$, SR$^a$, SOR$^a$, NR$^a$R$^b$, NR$^a$COR$^b$, NR$^a$CO$_2$R$^b$, CO$_2$R$^a$ or CONR$^a$R$^b$, where R$^a$ and R$^b$ are H, $C_{1-6}$alkyl, phenyl or trifluoromethyl; are tachykinin antagonists useful in therapy.

13 Claims, No Drawings

HETEROCYCLIC AMIDE DERIVATIVES AS TACHYKININ ANTAGONISTS

This application is a 371 of PCT/GB93/01415 filed Jul. 6, 1993.

This invention relates to a class of heterocyclic compounds, which are useful as tachykinin receptor antagonists.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
   Arg-Pro-Lys-Pro-Gln-Gln-Phe-Phe-Gly-Leu-Met-$NH_2$
Neurokinin A:
   His-Lys-Thr-Asp-Ser-Phe-Val-Gly-Leu-Met-$NH_2$
Neurokinin B:
   Asp-Met-His-Asp-Phe-Phe-Val-Gly-Lou-Met-$NH_2$ Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitus, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], and as anticonvulsants [Garant et al., Brain Research (1986) 382 372–8]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

Peptide tachykinin antagonists containing an indolyl or like moiety are disclosed in European patent applications nos. 0 394 989 and 0 482 539.

In view of their metabolic instability, peptide derivatives are likely to be of limited utility as therapeutic agents. It is for this reason that non-peptide tachykinin receptor antagonists are sought.

In essence, this invention provides a class of potent non-peptide tachykinin receptor antagonists.

The present invention provides a compound of formula (I), or a salt or prodrug thereof:

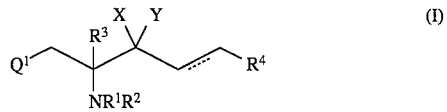

wherein $Q^1$ represents a phenyl group substituted by one or more halo; optionally substituted naphthyl; optionally substituted indolyl; optionally substituted benzthiophenyl; optionally substituted benzofuranyl; optionally substituted benzyl; or optionally substituted fluorenyl;

the dotted line represents an optional covalent bond;

one of X and Y represents H and the other of X and Y represents hydroxy or $C_{1-6}$alkoxy, or X and Y together form a group $=O$ or $=NOR^5$ where $R^5$ is H or $C_{1-6}$alkyl;

$R^1$ represents H or $C_{1-6}$alkyl.

$R^2$ represents $CO-W-R^6$ where W represents a bond or a saturated or unsaturated hydrocarbon chain of 1, 2, 3, 4, 5 or 6 carbon atoms and $R^6$ is an optionally substituted aromatic or non-aromatic azacyclic or azabicyclic group;

$R^3$ represents H, $C_{1-6}$alkyl or $C_{2-6}$alkenyl; and $R^4$ represents phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl.

For the avoidance of doubt, when the covalent bond represented by the dotted line is present, the compounds of formula (I) contain an olefinic double bond.

As used herein, the definition of each expression, when it occurs more than once in any structure, is intended to be independent of its definition elsewhere in the same structure.

The alkyl, alkenyl and alkynyl groups referred to with respect to any of the above formulae may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

When W represents a hydrocarbon chain of 2 or more carbon atoms, it may be straight or branched.

Where $Q^1$ represents optionally substituted fluorenyl, the fluorenyl group is linked through the bridgehead carbon atom, that is to say, C-9.

Where $Q^1$ represents optionally substituted naphthyl, indolyl, benzothiophenyl, benzofuranyl, benzyl or fluorenyl, suitable substituents include $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined. One or more substituents may be present and each may be located at any available ring position, except, where $Q^1$ is optionally substituted indolyl, the nitrogen atom. Where $Q^1$ is optionally substituted indolyl, suitable nitrogen substituents include $C_{1-6}$alkyl, optionally substituted phenyl($C_{1-4}$alkyl), $COOR^a$ or $CONR^aR^b$, wherein $R^a$ and $R^b$ are as above defined.

Suitable values of the group $Q^1$ include dihalophenyl such as 3,4-dichlorophenyl, indolyl such as 3-indolyl, naphthyl such as 2-naphthyl and 3-naphthyl, 9-fluorenyl, benzyl, benzothiophenyl such as 3-benzothiophenyl and benzofuranyl such as 3-benzofuranyl.

Preferably $Q^1$ is 3-indolyl, 3-benzothiophenyl or 3,4-dichlorophenyl, more preferably 3-indolyl.

Preferably the double bond is absent.

Preferably one of X and Y represents $C_{1-6}$alkoxy, such as methoxy, or X and Y together represent $=O$. More preferably X and Y together represent $=O$.

Preferably $R^1$ is H.

Suitable values for W include a bond, $CH_2$, $CH_2CH_2$, $CH=CH$, $CH_2CH_2CH_2$ and $CH_2CH_2CH_2CH_2$.

In one subgroup of compounds according to the invention, $R^2$ represents $CO(CH_2)_q R^6$, where q is 0, 1, 2, 3, 4, 5 or 6 and $R^6$ is as previously defined.

The aromatic or non-aromatic azacycle or azabicycle $R^6$ may contain one or more additional heteroatoms selected from N, O and S, or groups $NR^7$, where $R^7$ is H or $C_{1-6}$alkyl, and may be unsubstituted or substituted. Suitable substituents include $C_{1-6}$alkyl, $C_{1-6}$alkoxy, oxo, SH, $=S$, halo, trifluoromethyl, $NR^a R^b$, $NR^a COR^b$, $CONR^a R^b$, $CO_2 R^a$ and $CH_2 OR^a$, where $R^a$ and $R^b$ are as previously defined.

When $R^6$ represents an aromatic azacycle or azabicycle, suitable values of $R^6$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl, more preferably pyridyl such as 4-, 3- or 2-pyridyl.

When $R^6$ represents a non-aromatic azacycle or azabicycle, suitable values of $R^6$ include morpholinyl, piperdinyl, pyrrolidinyl, piperazinyl, methylpiperazinyl, azanorbornanyl, 3,4-pyridinecarboximido, azabicyclo[2.2.2]octanyl and azabicyclo[3.2.2]nonyl, preferably morpholinyl, piperazinyl, methylpiperazinyl, piperidinyl, pyrrolidinyl, 3,4-pyridinecarboximido, quinuclidinyl (azabicyclo[2.2.2]octanyl) or azabicyclo[3.2.2]nonyl.

Preferably $R^4$ represents substituted phenyl. Suitable phenyl substituents include nitro, trifluoromethyl, trimethylsilyl, bromo, chloro, fluoro, iodo, cyano, methyl, ethyl, cyclopropyl, t-butyl, vinyl, methoxy, phenoxy and amino. Suitably $R^4$ represents monosubstituted phenyl, such as 3-substituted phenyl, or, preferably, disubstituted phenyl, such as 3,5-disubstituted phenyl, when $R^4$ is 3-substituted phenyl, a particularly suitable substituent is t-butyl. More preferably, $R^4$ represents phenyl substituted by 1 or 2 groups selected from $C_{1-4}$alkyl, halo and trifluoromethyl.

Particularly preferred are compounds wherein $R^4$ represents 3,5-bis(trifluoromethyl)phenyl.

A particular subgroup of compounds according to the invention is represented by compounds of formula (Ia), and salts and prodrugs thereof:

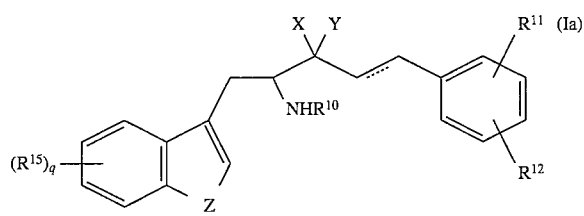

(Ia)

wherein X and Y are as defined for formula (I);

the dotted line represents an optional covalent bond;

Z represents O, S or $NR^{14}$ (where $R^{14}$ is H, $C_{1-6}$alkyl, optionally substituted phenyl($C_{1-4}$alkyl), $CO_2 R^a$ or $CONR^a R^b$, where $R^a$ and $R^b$ are as previously defined), preferably S or NH, more preferably NH;

$R^{10}$ is $CO-W-R^{16}$ where $R^{16}$ is imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl, indolyl, morpholinyl, piperdinyl, pyrrolidinyl, pyridosuccinimido, piperazinyl, methylpiperazinyl, azanorboranyl, azabicyclo[2.2.2]octanyl or azabicyclo[3.2.2] nonyl, preferably imidazolyl, pyridyl, morpholinyl, methylpiperazinyl, azabicyclo[2.2.2]octanyl or azabicyclo[3.2.2]nonyl and W is as previously defined, preferably a bond or a hydrocarbon chain of 1, 2 or 3 carbon atoms;

$R^{11}$ and $R^{12}$ each independently represent H, $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^a R^b$, $NR^a COR^b$, $NR^a CO_2 R^b$, $CO_2 R^a$ or $CONR^a R^b$, where $R^a$ and $R^b$ are as previously defined;

each $R^{13}$ may occupy any available carbon atom of the bicyclic ring system and independently represents $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^a R^b$, $NR^a COR^b$, $NR^a CO_2 R^b$, $CO_2 R^a$ or $CONR^a R^b$, where $R^a$ and $R^b$ are as previously defined; and n is 0, 1, 2 or 3, preferably 0.

Preferred are compounds of formula (Ia) wherein the optional covalent bond is absent.

A further subgroup of compounds according to the invention is represented by compounds of formula (Ib), and salts and prodrugs thereof:

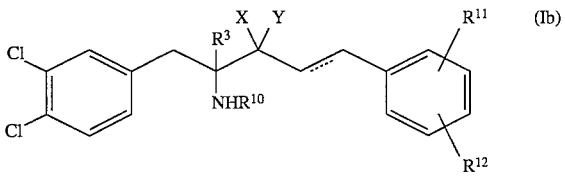

(Ib)

wherein $R^3$, $R^{10}$, $R^{11}$, $R^{12}$, X and Y are as previously defined and the dotted line represents an optional covalent bond.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when both $R^1$ and $R^2$ are other than hydrogen, the nitrogen atom to which they are attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention accordingly provides compounds of formula (I) and their pharmaceutically acceptable salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The substance P antagonising activity of the compounds described herein was evaluated using the human NK1R assay described in published European patent application no. 0 528 495. The method essentially involves determining the concentration of the test compound required to reduce by 50% the amount of radiolabelled substance P binding to human NK1R, thereby affording an $IC_{50}$ value for the test compound. The compounds of Examples 1–10, for example, were found to have $IC_{50}$ values less than 100 nM.

The invention also provides pharmaceutical compositions comprising a compound of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, including diabetic and chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I), or a salt or prodrug thereof, for use in therapy.

In the treatment of conditions involving actions of tachykinins released physiologically in response to noxious or other stimuli, a suitable dosage level is about 0.001 to 50 mg/kg per day, preferably about 0.005 to 10 mg/kg per day, and especially about 0.005 to 5 mg/kg per day. The compounds may be administered on a regimen of 1 to 4 times per day, preferably once daily.

According to a further or alternative aspect, the present invention provides a method of treatment of a human or animal subject suffering from or susceptible to a condition characterised by the presence of an excess of tachykinin which method comprises administering to a human or animal subject in need of such treatment an effective amount of a compound of formula (I), or a salt or prodrug thereof.

The present invention also provides the use of a compound of formula (I), or a salt or prodrug thereof, for the manufacture of a medicament for the treatment of conditions characterised by the presence of an excess of tachykinins.

Compounds of formula (I) may be prepared from intermediates of formula (II):

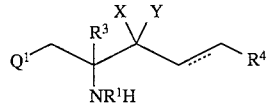

(II)

wherein $Q^1$, $R^3$, $R^4$, X, Y and—are as defined for formula (I), by reaction with a reagent suitable to introduce the group $R^2$.

Suitable reagents will be readily apparent to those skilled in the art and include, for example, carboxylic acids of formula $R^2$—OH, acyl halides of formula $R^2$—Hal, where Hal is halo, such as chloro, bromo or iodo. The reaction is preferably conducted in the presence of a base, such as a tertiary amine, for example, triethylamine, conveniently in a suitable organic solvent, such as, for example, dimethyl formamide.

Acids and acyl halides of formulae $R^2$—OH and $R^2$—Hal are commercially available or may be prepared by conventional methods, for example, as described in the accompanying examples or in Hely. Chim. Acta, 57, 2332 (1974).

Intermediates of formula (II) wherein X and Y together represent =O and the double bond is present may be prepared by reaction of an aldehyde of formula $R^4CHO$ with a compound of formula (III):

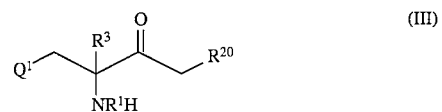

(III)

wherein $Q^1$, $R^1$ and $R^3$ are as defined for formula (I) and $R^{20}$ represents a group $PR^x_3$ or $PO(OR^x)_2$, wherein $R^x$ represents phenyl or $C_{1-10}$alkyl, in the presence of a base.

Suitable bases include alkali metal hydrides, such as, for example, sodium hydride, alkali metal carbonates, such as, for example, potassium carbonate, and strong orgainc bases such as, for example, 1,8-diazabicylo[5.4.0] undec-7-ene in the presence of anhydrous lithium chloride.

The reaction is conveniently effected in a suitable organic solvent, such as an ether, e.g. tetrahydrofuran, or acetonitrile, suitably at ambient temperature.

Compounds of formula (II) wherein one of X and Y represents H and the other represents hydroxy may be prepared from the corresponding compounds of formula (II) wherein X and Y together represent =O, by reduction.

Suitable reducing agents include, for example, hydride reducing agents such as lithium aluminium hydride and sodium borohydride.

The reaction is conveniently carried out in a suitable organic solvent, such as an ether, e.g. tetrahydrofuran, suitably at ambient temperature.

Compounds of formula (II) wherein one of X and Y represents H and the other represents $C_{1-6}$alkoxy may be prepared from the corresponding compounds of formula (II) wherein one of X and Y represents H and the other represents hydroxy, by alkylation.

Suitable alkylation procedures include treatment of an alcohol of formula (II) with an alkali metal hydride, such as sodium hydride, and a $C_{1-6}$alkylhalide. Suitable halides include, in particular, bromides and iodides.

The reaction is conveniently effected in an anhydrous organic solvent, for example, an ether, e.g. dimethoxyethane, suitably at ambient temperature.

Compounds of formula (II) wherein X and Y together represent =$NOR^5$ may be prepared from the corresponding compounds of formula (II) wherein X and Y together represent =O by the addition of hydroxylamine, or a derivative thereof. Compounds wherein $R^5$ is other than H may be prepared from the corresponding compounds wherein $R^5$ is H by alkylation, for example, using a diazo compound, such as diazomethane, or an alkyl halide or sulphate.

Compounds of formula (II) wherein the double bond is absent may be prepared from the corresponding unsaturated compounds of formula (II) by reduction.

Suitable reduction procedures include catalytic hydrogenation. Suitable hydrogenation catalysts include nobel metals, for example, platinum or palladium, or oxides thereof, which may be supported, for example, on charcoal. A preferred catalyst is Wilkinson's catalyst (tris(triphenylphosphine)rhodium(I)chloride).

The reaction is conveniently effected in a suitable organic solvent, such as an ether, e.g. tetrahydrofuran, an alcohol, e.g. ethanol, or an ester, e.g. ethyl acetate, suitably at ambient temperature.

Compounds of formula (III) may be prepared from compounds of formula (IV)

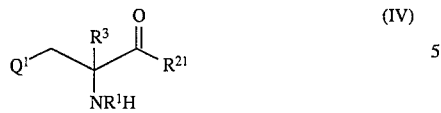

wherein $Q^1$, $R^1$ and $R^3$ are as defined for formula (I) and $R^{21}$ represents an alkoxy or a suitably substituted amino group, such as a group $NR^YOR^Z$, where $R^Y$ and $R^Z$ represent alkyl, in particular a group $NCH_3(OCH_3)$, by reaction with a compound of formula $CH_3PO(OR^X)_2$, where $R^X$ is an alkyl group, in the presence of a base.

Suitable reaction procedures will be readily apparent to the skilled person and examples thereof are described in the accompanying Examples.

Suitable bases of use in the reaction include alkyl lithiums, such as butyl lithiums.

Compounds of formula (IV) are commercially available or may be prepared using standard procedures well known to the skilled person in the art. The compounds of formula (IV) are amino acid derivatives. Syntheses of amino acids and derivatives thereof are well documented and are described, for example, in *Chemistry and Biochemistry of the Amino Acids*, ed. G. C. Barrett, Chapman and Hall, 1985.

Where the above-described processes for the preparation of the compounds according to the invention give rise to mixtures of stereoisomers, these isomers may be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following non-limiting Examples illustrate the preparation of compounds according to the invention.

EXAMPLE 1

5-(3,5-Bistrifluoromethylphenyl)-1-(3-indolyl)-2-((N-morpholinyl)acetamido)-3-pentanone Hydrochloride (a) N-Methoxy-N-methyl2-t-butyloxycarbonylamino-3-(3-indolyl)propionamide N-δ-BOC-L-tryptophan (100 g) was dissolved in dimethyl formamide (800 ml) and triethylamine (101 g) was added. The reaction was cooled to −30° C. and isobutyl chloroformate (42.5 ml) was added, maintaining the internal temperature to below −20° C. The reaction was stirred for 15 minutes before adding N,O-dimethyl hydroxylamine hydrochloride (64 g) and then diluting the reaction with dichloromethane (1 l), maintaining the internal temperature below 0° C. The reaction was stirred for 15 minutes, poured into ethyl acetate (3l) and washed with 10% citric acid (1 l), water (3×1 l), saturated sodium bicarbonate (1 l) and water (1 l). The organic phase was dried (MgSO$_4$), filtered, and evaporated until crystallisation ensued. The suspension was diluted with petroleum ether, filtered and dried to yield the title compound; mp=129°–130° C.; $^1$H NMR (360 MHz, D$_6$ DMSO) δ10.80 (1H, s); 7.51 (1H, d, J=7 Hz); 7.33 (1H, d, J=7 Hz); 7.16 (1H, s); 7.08–6.97 (3H, m); 4.62–4.58 (1H, m); 3.72 (3H, s); 3.34 (3H, s); 3.02–2.81 (2H, m); 1.31 (9H, s).

(b) 2-t-Butyloxycarbonylamino-1-(3-indolyl)-4-dimethylphosphono-3-butanone

Dimethyl methane phosphonate (205 g) was dissolved in tetrahydrofuran (800 ml), cooled to −70° C.; and then treated with n-butyllithium (1.6M in hexane, 900 ml), maintaining the internal temperature of the reaction at below −55° C. The reaction was stirred for one hour before adding the product of part (a) (90 g). The reaction was stirred at −70° C. for 30 minutes before quenching with saturated ammonium chloride. The resulting mixture was extracted with ethyl acetate and the organic extract was washed with water (5×500 ml), dried (MgSO$_4$) and evaporated. The residue was purified on silica (eluting with ethyl acetate) to yield the title compound as an oil; $^1$H NMR (360 MHz, CDCl$_3$) δ10.84 (1H, s), 7.56 (1H, d, J=7 Hz), 7.33 (1H, d, J=7 Hz), 6.98 (1H, t, J=7 Hz), 434–431 (1H, m), 3.63 (6H, d, J=11 Hz), 3.39 (2H, d, J=22 Hz), 3.19–3.11 (1H, m), 2.91–2.84 (1H, m); found: C, 55.73, 6.34; N, 6.80; C$_{19}$H$_{27}$N$_2$O$_6$P requires C, 55.60; H, 6.63; N, 6.82%.

(c) 5-(3,5-Bistrifluoromethylphenyl)-2-t-butyloxycarbonylamino-1-(3-indolyl)-4-penten-3-one A solution of the product of part (b) (69.0 g) in acetonitrile (600 ml) was stirred with diisopropylethylamine (43.3 g), and anhydrous lithium chloride (14.13 g) for 30 minutes before adding 3,5-bistrifluoromethylbenzaldehyde (55 g) in acetonitrile (200 ml). The reaction was stirred for two hours then the solvent was removed and the residue partitioned between ethyl acetate and water. The organic phase was washed with 10% citric acid (500 ml), water (500 ml), saturated sodium bicarbonate (500 ml) and water (500 ml). The solution was dried (MgSO$_4$), filtered and evaporated. The residue was purified by column chromatography on silica using ethyl acetate/petroleum ether (1:4) to yield the title compound as a pale yellow solid, mp=137°–138° C.; found: C, 59.23; H, 4.79; N, 5.35; C$_{26}$H$_{24}$F$_6$N$_2$O$_3$ requires C, 59.32; H, 4.60; N 5.32%.

(d) 5-(3,5-Bistrifluoromethylphenyl)-2-t-butyloxycarbonylamino-1-(3-indolyl)-3-pentanone The product of part (c) was heated under reflux with tri-n-butyltin hydride (51.12 g) in toluene for 20 hours. The reaction was cooled and purified by column chromatography on silica using ethyl acetate/petroleum ether (1:4) to yield the title compound as a white solid (37.1 g), mp=138°–140° C.: found: C, 59.23; H, 4.90; N, 5.28; C$_{26}$H$_{24}$F$_6$N$_2$O$_3$ requires C, 59.09, H, 4.96; N, 5.30%.

(e) 2-Amino-5-(3,5-bistrifluoromethylphenyl)-1-(3-indolyl)-3-pentanone Hydrochloride The product of part (d) was treated with ethereal hydrogen chloride for one hour. The precipitated white solid was filtered and dried, mp=84°–86° C.; found: C,54.40; H, 4.25; N,6.10; C$_{21}$H$_{18}$F$_6$N$_2$O. HCl requires C, 54.26; H, 4.12; N, 6.03%.

(f) 5-(3,5-bistrifluoromethylphenyl)-1-(3-indolyl)-2-((N-morpholinyl)acetamido)-3-pentanone Hydrochloride Potassium 2-(N-morpholinyl)acetate (0.2 g) and triethylamine (0.1 g) were dissolved in dry dimethylformamide and cooled to −30° C. before adding isobutylchloroformate (0.147 g). The reaction was stirred for 20 minutes before adding the product of example 1(e). The reaction was stirred for 3 hours, poured into water and then partitioned between ethyl acetate and water. The organic phase was washed with water (100 ml), sodium bicarbonate (100 ml) and water (100 ml). The organic extract was dried ($MgSO_4$), filtered and evaporated. The residue was purified by column chromatography on silica using ethyl acetate. The resulting oil was treated with ethereal hydrogen chloride to yield the title compound as a white solid, mp=83°–86° C.; found: C, 53.67; H, 4.89; N, 6.86 $C_{27}H_{27}F_6N_3O_3$. HCl. 0.5 $H_2O$ requires C, 53.96; H, 4.86; N, 6.99%.

EXAMPLE 2

5-(3,5-Bistrifluoromethylphenyl)-1-(3-indolyl)-2-((4-pyridyl)acetamido)-3-pentanone Hydrochloride 4-Pyridylacetic acid (210 mg) was suspended in a solution of triethylamine (234 mg) in dimethylformamide (4 ml) and dichloromethane (5 ml). Carbonyl diimidazole (196 mg) was added to the suspension and stirred for 0.5 hours before adding the compound of Example 1(e) (500 mg). The reaction was stirred for 12 hours, poured into ethyl acetate and washed with water. The organic layer was dried ($MgSO_4$), evaporated and purified by silica chromatography using dichloromethane/methanol (98.2). The oil obtained was treated with ethereal hydrogen chloride to yield the title compound as a solid, mp=88°–90° C.; found: C, 55.79; H, 4.40; N, 6.78 $C_{28}H_{23}F_6N_3O_2$. HCl. $H_2O$ requires C, 55.87; H, 4.35; N, 6.98%.

EXAMPLE 3

5-(3,5-Bistrifluoromethylphenyl)-2-((4-imidazolyl)acetamido)-1-(3-indolyl)-3-pentanone Hydrochloride Prepared from the compound of Example 1(e) in a similar manner to Example 2 using imidazole-4-acetic acid to give the title compound as a white solid, mp=103°–106° C.; found C, 51.95; H, 4.33; N, 9.29; $C_{26}H_{22}F_6N_4O_2$. HCl. 1.5 $H_2O$ requires C, 52.05; H, 4.37; N, 9.34%.

EXAMPLE 4

5-(3,5-Bistrifluoromethylphenyl)-1-(3-indolyl)-2-((3-pyridyl)acetamido)-3-pentanone Hydrochloride Prepared from the compound of Example 1(e) in a similar manner to Example 2 using 3-pyridylacetic acid to give the title compound as a solid, mp=90°–92° C.; found: C, 56.48; H, 4.47; N, 7.10; $C_{28}H_{23}F_6N_3O_2$. HCl. 0.5 $H_2O$ requires C, 56.72; H, 4.25; N, 7.09%.

EXAMPLE 5

5-(3,5-Bistrifluoromethylphenyl)-1-(3-indolyl)-2-((2-pyridyl)acetamido)-3-pentanone Hydrochloride Prepared from the compound of Example 1(e) in a similar manner to Example 2 using 2-pyridylacetic acid to give the title compound as a solid, mp=92°–94° C.; found: C, 56.72; H, 4.35; N, 6.91; $C_{28}H_{23}F_6N_3O_2$.HCl.0.5$H_2O$ requires C, 56.72; H, 4.25 N, 7.09%.

EXAMPLE 6

5-(3,5-Bistrifluoromethylphenyl)-1-(3-indolyl)-2-((4-methyl piperazinyl)acetamido)-3-pentanone Hydrochloride Prepared from the compound of Example 1(e) in a similar manner to Example 1(f) using potassium 2-(4-methylpiperazinyl) acetate to give the title compound as a white solid, mp=120°–122° C.; found C, 49.35; H, 5.04; N, 8.09; $C_{28}H_{30}F_6N_4O_2$. 2 HCl. 2$H_2O$ requires C, 49.64; H, 5.36; N, 8.27%.

EXAMPLE 7

5-(3,5-Bistrifluoromethylphenyl)-1-(3-indolyl)-2-(quinuclidine-4-carboxamido)-3-pentanone Hydrochloride Quinuclidine-4-carboxylic acid (Helv. Chim Acta, 57, 2332, (1974) (110 mg) was heated with thionyl chloride (2 ml) for 2 hours. The solvent was removed and the residue was azeotroped with toluene (3×10 ml) and then dissolved in dichloromethane (10 ml). The compound of Example 1(e) (325 ml) was dissolved in a mixture of dichloromethane (10 ml) and triethylamine (200 mg) and added to the above solution. The reaction was stirred for 1 hour, poured into ethyl acetate and washed with potassium carbonate solution. The organic solution was dried, evaporated and purified by alumina chromatography using dichloromethane/methanol (99:1). The oil obtained was treated with ethereal hydrogen chloride to yield the title compound as a white solid mp=183°–184° C.; found: C, 55.97; H, 5.25; N, 6.85; $C_{29}H_{29}F_6N_3O_2$.HCl.$H_2O$ requires C, 56.18; H, 5.20; N, 6.78%.

EXAMPLE 8

5-(3,5-Bistrifluoromethylphenyl)-1-(3-indolyl)-2-(3-(piperidin-1-yl) propionamido)-3-pentanone Prepared from the compound of Example 1(e) in a similar manner to Example 7 using 1-piperidinopropionic acid and obtained as a white solid, mp 141° C.; found: C, 61.26; H, 5.46; N, 7.35. $C_{29}H_{31}N_3O_2F_6$ requires C: 61.37; H, 5.50; N, 7.40.

EXAMPLE 9

5-(3,5-Bistrifluoromethylphenyl)-1-(3-indolyl)-2-(4-(3-(3-azabicyclo[3.2.2]nonyl))butyramido)-3-pentanone Hydrochloride a) Ethyl-4-(3-(3-azabicyclo[3.2.2]nonyl)) butyrate To a solution of 3-azabicyclo[3.2.2]nonane (0.5 g) in tetrahydrofuran (5 ml) was added triethylamine (0.6 ml) followed by ethyl 4-bromobutyrate (0.63 ml). The solution was stirred for 16 hours under reflux, cooled and concentrated in vacuo. The residue was partitioned between ethyl acetate and water and the organic solution separated, dried ($Na_2SO_4$) and concentrated. The residue was purified by chromatography on silica gel eluting with diethyl ether-petroleum ether (1:9) to give the title compound.

b) 5-(3,5-Bistrifluoromethylphenyl)-1-(3-indolyl)-2-(4-(3-(3-azabicyclo [3.2.2]nonyl))butyramido)-3-pentanone Hydrochloride To a solution of the product of part a) (0.67 g) in water (3 ml) and ethanol (1.5 ml) was added 2N sodium hydroxide solution (1.4 ml). The solution was heated under reflux for 2 hours then cooled and adjusted to pH1 with dilute hydrochloric acid. The solution was freeze dried and the resulting solid added to dimethylformamide (15 ml) containing 1-(3-dimethylaminopropyl)-3-ethylcarbodiimide hydrochloride (0.54 g). After stirring for 30 minutes at 0° C., a solution of 5-(3,5-bistrifluoromethylphenyl)-1-(3-indolyl)-2-amino-3-pentanone hydrochloride and triethylamine (0.3 ml) in dimethylformamide (5 ml) was added and stirred for 16 hours at 25° C. Ethyl acetate was added and the solution washed with water (3×), dried ($Na_2SO_4$) and concentrated. The residue was purified by chromatography on silica gel eluting with methanol-dichloromethane (1:19) then treated with ethereal hydrogen chloride to give the title compound, mp 101°–104° C.; found: C, 56.90; H, 5.95; N, 5.67. $C_{33}H_{37}F_6N_3O_2.HCl.2H_2O$ requires C, 57.09; H, 6.09; N, 6.05.

EXAMPLE 10

5-(3,5-Bistrifluoromethylphenyl)-1-(3-benzo[b]thienyl)-2-((4-pyridyl)acetamido)-3-pentanone a) 3-(3-Benzo[b]thienyl)-2-t-butyloxycarbonylamino propionic acid 2-Amino-3-(3-benzo[b]thienyl)propionic acid (*Int. J. Peptide Protein Res.*, (1987), 29, 118) (22.9 g) and sodium carbonate (27.6 g) were added to a mixture of water (350 ml) and 1,4-dioxane (150 ml). Di-t-butyldicarbonate (34.1 g) was added to the mixture and the reaction was stirred for 16 hours and washed with ether (500 ml). The reaction mixture was acidified to pH3 with solid citric acid and extracted with ethyl acetate to yield the title compound (31.5 g).

b) Methyl 3-(3-benzo[b]thienyl-2-t-butyloxy carbonyl amino propionate

The product of Example 9(a) (31.5 g) and Cesium carbonate (15.93 g) were dissolved in methanol and the solvent was removed by evaporation. The residue was dissolved in dimethylformamide and iodomethane (27.8 g) was added. The reaction was stirred for 16 hours then the solvent was removed and the residue partitioned between ethyl acetate and water. The organic extract was washed with sodium bicarbonate solution and water, dried ($MgSO_4$), and evaporated. The residue was purified by column chromatography on silica using ethyl acetate/petroleum ether (1:4) to yield the title compound (27.3 g).

c) 5-(3,5-Bistrifluoromethylphenyl)-1-(3-benzo[b]thienyl)-2-((4-pyridyl)acetamido)-3-pentanone Prepared by the methods of Examples 1(b)–1(e) and 2 starting with the compound of Example 10(b) instead of the compound of Example 1(a). Mp 184°–187° C.; found C, 56.06; H, 4.03; N, 4.77. $C_{28}H_{22}F_6N_2O_2S.HCl$ requires C, 55.96; H, 3.86; N, 4.66.

EXAMPLE 11

5-(3,5-Bistrifluoromethylphenyl)-1-(3,4-dichlorophenyl)-2-((4-pyridyl)acetamido)-3-pentanone Prepared by the method of Example 10 starting with 3,4-dichlorophenylalanine. Mp 142°–144° C.; found: C, 49.96; H, 3.63; N, 4.36. $C_{26}H_{20}Cl_2F_6N_2O_2.HCl.0.5H_2O$ requires C, 50.14; H, 3.56; N, 4.50.

EXAMPLE 12

5-(3,5-Bistrifluoromethylphenyl)-1-(3,4-dichlorophenyl)-2-(quinuclidine-4-carboxamido)-3-pentanone Hydrochloride Prepared by the methods of Examples 7 and 14. Mp 50°–530° C.; found: C, 49.89; H, 4.53; N, 4.30. $C_{27}H_{26}Cl_2F_6N_2O_2.HCl.H_2O$ requires C, 49.90; H, 4.50; N, 4.37.

EXAMPLE 13

5-(3,5-Bistrifluoromethylphenyl)-1-(3-indolyl)-2-((4-pyridyl)acetamido)-3-oximinopentane The compound of Example 2 (1.0 g) in methanol (2.0 ml) was treated with hydroxylamine hydrochloride (0.5 g) and sodium acetate (1.5 g) for 16 hours. The solution was concentrated in vacuo and the residue partitioned between ethyl acetate and water. The ethyl acetate solution was separated, dried and concentrated and the residue crystallised from ethyl acetate/petroleum other to give the title compound, mp 196°–1980° C. Found: 59.87; H, 4.39; N, 9.93. $C_{28}H_{24}F_6N_4O_2$ requires C, 59.79; H, 4.30; N, 9.96.

EXAMPLE 14

5-(3,5-Bistrifluoromethylphenyl)-1-(3,4-dichlorophenyl)-2-4-(3-(3-azabicyclo[3.2.2]nonyl))butyramido)-3-pentanone Hydrochloride Prepared by the methods of Examples 9 and 14. Mp 90°–930° C. Found: C, 51.58; H, 5.42; N, 3.83. $C_{31}H_{34}Cl_2F_6N_2O_2.HCl.2H_2O$ requires C, 51.43; H, 5.43; N, 3.87.

EXAMPLE 15

5-(3,5-Bistrifluoromethylphenyl)-1-(3-indolyl)-2-((4-pyridyl)acetamido)-3-pentanol A solution of the compound of Example 2 (360 mg) in ethanol (10 ml) was treated with sodium borohydride (100 mg) for 1 hour. The solution was concentrated in vacuo and the residue partitioned between ethyl acetate and ammonium chloride solution. The organic solution was dried and evaporated to give a white solid. Crystallisation from ethyl acetate-diethyl ether gave the title compound as a single diastereomer, mp 213°–214° C.; found: C, 60.97; H, 4.58; N, 7.47. $C_{28}H_{25}F_6N_3O_2$ requires C, 61.20; H, 4.59; N, 7.65.

Further crystallisation of the mother liquors from above gave the title compound as a mixture of diastereomers.

EXAMPLE 16

5-(3,5-Bistrifluoromethylphenyl)-1-(3-indolyl)-2-(4-(1-pyrrolidinyl)butyramido)-3-pentanone The title compound was prepared from pyrrolidine-1-butyric acid and the compound of Example 1e) using 1-(3-dimethylaminopropyl)-3-ethylcarbodiimide hydrochloride as coupling agent by the method of Example 9. Mp 99°–100° C.; found: C, 61.70; H, 5.48;N, 7.36. $C_{29}H_{31}F_6N_3O_2$ requires C, 61.37; H, 5.51; N, 7.40.

EXAMPLE 17

5-(3,5-Bistrifluoromethylphenyl)-1-(3-indolyl)-2-(4-(4-morpholinyl)butyramido)-3-pentanone Hydrochloride Prepared by the method of Example 16 using 4-morpholine butyric acid. Mp 64°–65° C.; found: C, 53.84; H, 5.44; N, 6.32. $C_{29}H_{31}F_6N_3)_3$. $HCl.1.5H_2O$ requires C, 53.83;H, 5.45;N, 6.49.

EXAMPLE 18

5-(3,5-Bistrifluoromethylphenyl)-1-(3-indolyl)-2-(3-(3-pyridyl)acrylamido)-3-pentanone Prepared by the method of Example 16 using 3-(3-pyridyl)acrylic acid. Mp 138°–139° C.; found C, 62.66; H, 4.01; N, 7.54. $C_{29}H_{23}F_6N_3O_2$ requires C, 62.25; H, 4.14; N, 7.51.

EXAMPLE 19

5-(3,5-Bistrifluoromethylphenyl)-1-(3-indolyl)-2-(3-(3-pyridyl)propionamido)-3-pentanone A solution of 3-pyridylacrylic acid (900 mg) in ethanol (30 ml) was shaken under hydrogen gas at 30 psi for 2.5 hours over 10% Pd-C (100 mg). The solution was filtered and concentrated under reduced pressure to give a colourless solid which was dried under high vacuum. The resulting solid with the compound of Example 1e), by the method of Example 7, gave the title compound, mp 123°–124° C.; found: C, 62.11; H, 4.16; N, 7.25. $C_{29}H_{25}F_6N_3O_2$ requires C, 62.03; H, 4.49; N, 7.48.

EXAMPLE 20

5-(3,5-Bistrifluoromethylphenyl)-1-(3-indolyl)-2-(3-(4-pyridyl)acrylamido)-3-pentanone Hydrochloride a) 4-pyridylacrylic acid A mixture of potassium carbonate (22 g), triethylphosphonoacetate (22.6 ml) and 4-pyridylcarboxaldehyde (11 g) in tetrahydrofuran (110 ml) was heating under reflux for 3 hours under an atmosphere of argon. The reaction was cooled, diluted with ethyl acetate, washed with water, dried ($K_2CO_3$) and concentrated in vacuo. The residue was diluted with petroleum ether and the resulting solid filtered and dried in vacuo. A solution containing a portion of the foregoing solid (2.1 g) in tetrahydrofuran (15 ml) and 4N aqueous sodium hydroxide (20 ml) was stirred for 16 hours. Ethyl acetate (30 ml) was added followed by acetic acid until the aqueous solution reached pH 7. The ethyl acetate solution was separated, dried ($MgSO_4$) concentrated and the residue crystallised from diethyl ether-petroleum ether to give the title compound.

b) 5-(3,5-Bistrifluoromethylphenyl)-1-(3-indolyl)-2-(3-(4-pyridyl)acrylamido)-3-pentanone Hydrochloride Prepared from 4-pyridylacrylic acid by the method of Example 16. Mp 122°–126° C.; found C, 58.08; H, 3.92; N, 6.79 $C_{29}H_{23}F_6N_3O_2$ HCl requires C, 58.45; H, 4.06; N, 7.05.

EXAMPLE 21

5-(3,5-Bistrifluoromethylphenyl)-1-(3-indolyl)-2-(3-(4-pyridyl)propionamido)-3-pentanone 4-Pyridylacrylic acid was hydrogenated by the method of Example 19 and reacted with the compound of Example 1e) by the method of Example 16 to give the title compound, mp 108° C.; found: C, 61.89;H, 4.31; N, 7.28. $C_{29}H_{25}F_6N_3O_2$ requires C, 62.03; H, 4.49; N, 7.48.

EXAMPLE 22

5-(3,5-Bistrifluoromethylphenyl)-1-(3-indolyl)-2-(3-(4-piperidinyl)propionamido)-3-pentanone Hydrochloride a) 3-(4-(1-$^t$Butyloxycarbonyl)piperidinyl) propionic acid To a solution of ethyl isonipecotate (17.1 g) in dichloromethane (60 ml) at 4° C. was added di-$^t$butyldicarbonate (24 g) with stirring. After 10 minutes the solvent was removed under reduced pressure and the residue dried under high vacuum, then dissolved in dichloromethane (100 ml). To this solution, under an atmosphere of argon at −78° C., was added diisobutyl aluminum hydride (110 ml of a 1.0M solution in toluene). After stirring for 1 hour, 2N hydrochloric acid (55 ml) was added dropwise and the mixture allowed to warm to 20° C., then diluted with ethyl acetate. The ethyl acetate solution was separated off, dried ($K_2CO_3$) and concentrated. The resulting residue was reacted with triethylphosphonoacetate and then sodium hydroxide by the method of Example 20a), then hydrogenated by the method of Example 19 to give the title compound which was crystallised from hot petroleum ether (bp 60°–80° C.).

b) 5-(3,5-Bistrifluoromethylphenyl)-1-(3-indolyl)-2-(3-(4-piperidinyl)propionamido)-3-pentanone Hydrochloride The compound of part a) (476 mg) in dry benzene (5 ml) was treated with oxalyl chloride (0.16 ml) until evolution of gas ceased. The solution was concentrated in vacuo and dissolved in dichloromethane (10 ml) with the compound of Example 1e) (740 mg) and triethylamine (0.56 ml). After stirring 1 hour aqueous sodium bicarbonate was added and the mixture extracted with dichloromethane which was then dried ($Na_2SO_4$) and concentrated. The residue was purified by chromatography on silica gel (eluant ethyl acetate-petroleum ether 2:3) then treated with ethereal hydrogen chloride for 16 hours. After removal of the solvent under reduced pressure, trituration with diisopropyl ether gave the title compound, mp 124°–126° C.; found: C, 57.31; H, 5.55; N, 6.53. $C_{29}H_{31}F_6N_3O_2$. HCl requires C,57.66; H, 5.43; N, 6.96.

EXAMPLE 23

5-(3,5-Bistrifluoromethylphenyl)-1-(3-indolyl)-2-(4-piperidinecarboxamido)-3-pentanone Hydrochloride The compound of Example 1e) was reacted with N-$^t$butoxycarbonylnipecotic acid by the method of Example 2. The resulting material was treated with ethereal hydrogen chloride for 16 hours then concentrated and crystallised from methanolethyl acetate to give the title compound, mp 209°–213° C.; found: C, 55.82; H, 4.75; N, 6.89. $C_{27}H_{27}F_6N_3O_2$. $HCl.0.25H_2O$ requires C, 55.87; H, 4.95; N, 7.24.

EXAMPLE 24

5-(3,5-Bistrifluoromethylphenyl)-1-(3-indolyl)-2-(3-(1-piperazinyl)ureido)-3-pentanone The compound of Example 1(c) (400 mg) in tetrahydrofuran (10 ml) was treated with triethylamine (0.12 ml) and 4-nitrophenylchloroformate (174 mg) for 1 hour. The solvent was removed in vacuo and the residue partitioned between ethyl acetate and water. The organic solution was dried ($Na_2SO_4$) and concentrated to give a solid which was dissolved in dichloromethane (15 ml). 'Butyl-1-piperazine carboxylate (156 mg) was added and the solution stirred under an atmosphere of nitrogen overnight. The reaction was diluted with dichloromethane, washed with water, dried ($Na_2SO_4$) and concentrated to give an oil which was purified by chromatography on silica gel eluting with ethyl acetate-petroleum ether (1:1). The resulting product was treated with ethereal hydrogen chloride for 16 hours then the solution was evaporated and the residue crystallised from diethyl ether-petroleum ether to give the title compound, mp 120°–122 °C.; found: C, 51.86; H, 4.97; N, 8.85. $C_{26}H_{26}F_6N_4O_2 \cdot HCl \cdot 1.5H_2O$ requires C, 51.70; H, 5.00; N, 9.27.

EXAMPLE 25

5-(3,5-Bistrifluoromethylphenyl)-1-(3-indolyl)-2-(4-pyridinecarboxamido)-3-pentanone The title compound was prepared using pyridine-4-carboxylic acid by the method of Example 9(b). Mpt 72°–74° C.; found: C, 59.63; H, 4.06; N, 7.62. $C_{27}H_{21}F_6N_3O_2 \cdot 0.5H_2O$ requires C, 59.78; H, 4.09; N, 7.75.

EXAMPLE 26

5-(3,5-Bistrifluoromethylphenyl)-1-(3-indolyl)-2-(2-(N-(3,4-pyridinedicarboximido))acetamido)-3-pentanone The title compound was prepared using N-carboxymethyl-3,4-pyridinedicarboximide by the method of Example 9(b). Mpt 144°–145° C.; found: C, 58.64; H, 3.57; N, 8.69. $C_{30}H_{22}F_6N_4O_4$ requires C, 58.45; H, 3.60; N, 9.09.

The following examples illustrate pharmaceutical compositions according to the invention.

| EXAMPLE 27A Tablets containing 1–25 mg of compound | Amount mg | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |
| EXAMPLE 27B Tablets containing 26–100 mg of compound | | | |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

| EXAMPLE 28 Parenteral injection | Amount mg |
|---|---|
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

| EXAMPLE 29 Topical formulation | Amount mg |
|---|---|
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

What is claimed is:

1. A compound of formula (I):

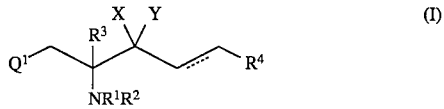

wherein

Q$^1$ represents indolyl optionally substituted by one or more groups selected from $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$, $CONR^aR^b$ and, optionally substituted at the indolyl nitrogen atom by a group selected from $C_{1-6}$alkyl, phenyl ($C_{1-4}$alkyl) optionally substituted on the phenyl ring by one or more of the above substituents, $COOR^a$ or $CONR^aR^b$, where $R^a$ and $R^b$ independently represent H, $C_{1-6}$alkyl, phenyl or trifluoromethyl;

the dotted line represents an optional covalent bond;

one of X and Y represents H and the other of X and Y represents hydroxy or $C_{1-6}$alkoxy, or X and Y together form a group =O or =NOR$^5$ where R$^5$ is H or $C_{1-6}$alkyl;

R$^1$ represents H or $C_{1-6}$alkyl;

R$^2$ represents CO—W—R$^6$ where W represents a bond or a saturated or unsaturated hydrocarbon chain of 1, 2, 3, 4, 5 or 6 carbon atoms and R$^6$ is imidazolyl, pyridyl, morpholinyl or pyrrolidinyl and each of which may be optionally substituted by $C_{1-6}$alkyl, $C_{1-6}$alkoxy, oxo, SH, =S, halo, trifluoromethyl, $NR^aR^b$, $NR^aCOR^b$, $CONR^aR^b$, $CO_2R^a$ and $CH_2OR^a$;

R$^3$ represents H, $C_{1-6}$alkyl or $C_{2-6}$alkenyl; and

R$^4$ represents phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$; or a salt or prodrug thereof.

2. A compound as claimed in claim 1 wherein $R^2$ represents $CO(CH_2)_qR^6$ where q is 0, 1, 2, 3, 4, 5 or 6 and $R^6$ is as defined for formula (I).

3. A compound as claimed in claim 1 wherein $Q^1$ is 3-indolyl.

4. A compound as claimed in claim 1 wherein the optional covalent bond is absent.

5. A compound as claimed in claim 1 wherein one of X and Y is H and the other of X and Y is $C_{1-6}$alkoxy; or X and Y together from a group =O.

6. A compound as claimed in claim 1 wherein $R^1$ is H.

7. A compound as claimed in claim 1 wherein $R^4$ represents phenyl substituted by 1 or 2 groups selected from $C_{1-4}$alkyl, halo and trifluoromethyl.

8. A compound as claimed in claim 1 selected from:

5-(3,5-bistrifluoromethylphenyl)-1-(3-indolyl)-2-((N-morpholinyl)acetamido)-3-pentanone;

5-(3,5-bistrifluoromethylphenyl)-1-(3-indolyl)-2-((4-pyridyl)acetamido)-3-pentanone;

5-(3,5-bistrifluoromethylphenyl)-2-((4-imidazolyl)acetamido)-1-(3-indolyl)-3-pentanone;

5-(3,5-bistrifluoromethylphenyl)-1-(3-indolyl)-2-((3-pyridyl)acetamido)-3-pentanone;

5-(3,5-bistrifluoromethylphenyl)-1-(3-indolyl)-2-((2-pyridyl)acetamido)-3-pentanone;

5-(3,5-bistrifluoromethylphenyl)-1-(3-indolyl)-2-((4-pyridyl)acetamido)-3-oximinopentane;

5-(3,5-bistrifluoromethylphenyl)-1-(3-indolyl)-2-((4-pyridyl)acetamido)-3-pentanol;

5-(3,5-bistrifluoromethylphenyl)-1-(3-indolyl)-2-(4-(1-pyrrolidinyl)butyramido)-3-pentanone;

5-(3,5-bistrifluoromethylphenyl)-1-(3-indolyl)-2-(4-(4-morpholinyl)butyramido)-3-pentanone;

5-(3,5-bistrifluoromethylphenyl)-1-(3-indolyl)-2-(3-(3-pyridyl)acrylamido)-3-pentanone;

5-(3,5-bistrifluoromethylphenyl)-1-(3-indolyl)-2-(3-(3-pyridyl)propionamido)-3-pentanone;

5-(3,5-bistrifluoromethylphenyl)-1-(3-indolyl)-2-(3-(4-pyridyl)acrylamido)-3-pentanone;

5-(3,5-bistrifluoromethylphenyl)-1-(3-indolyl)-2-(3-(4-pyridyl)propionamido)-3-pentanone;

5-(3,5-bistrifluoromethylphenyl)-1-(3-indolyl)-2-(4-pyridinecarboxamido)-3-pentanone;

5-(3,5-bistrifluoromethylphenyl)-1-(3-indolyl)-2-(2-(N-(3,4-pyridinecarboximido))acetamido)-3-pentanone;

and salts and prodrugs thereof.

9. A pharmaceutical composition comprising a compound as claimed in claim 1 in association with a pharmaceutically acceptable carrier.

10. A method for the treatment or prevention of a physiological disorder associated with an excess of tachykinins, which method comprises administration to a patient in need thereof of a tachykinin-reducing amount of a compound according to claim 1.

11. A method according to claim 10 for the treatment or prevention of pain or inflammation.

12. A method according to claim 10 for the treatment or prevention of migraine.

13. A method according to claim 10 for the treatment or prevention of arthritis.

* * * * *